United States Patent
Ryu et al.

[11] Patent Number: 5,857,979
[45] Date of Patent: Jan. 12, 1999

[54] METHOD FOR ANALYZING ELECTROENCEPHALOGRAM USING CORRELATION DIMENSION

[75] Inventors: Chang-Su Ryu; Seon-Hee Park; Seung-Hwan Kim, all of Daejeon, Rep. of Korea

[73] Assignee: Electronics and Telecommunications Research Institute, Daejeon, Rep. of Korea

[21] Appl. No.: 892,940

[22] Filed: Jul. 15, 1997

[30] Foreign Application Priority Data

Dec. 9, 1996 [KR] Rep. of Korea .................. 1996-63157

[51] Int. Cl.$^6$ ................................. A61B 5/0476
[52] U.S. Cl. ............................................. 600/544
[58] Field of Search ............................ 600/544; 128/920, 128/923

[56] References Cited

U.S. PATENT DOCUMENTS 5,687,724  11/1997  Jewett et al. ............................ 600/544

OTHER PUBLICATIONS

A. Babloyantz et al., "Evidence of Chaotic Dynamics of Brain Activity During the Sleep Cycle", Physics Letters, vol. 111A, No. 3, 2 Sep. 1985, pp. 152–156.

*Primary Examiner*—William E. Kamm
*Assistant Examiner*—Kennedy J. Schaetzle
*Attorney, Agent, or Firm*—Jacobson, Price, Holman & Stern, PLLC

[57] ABSTRACT

This invention provides a method for analyzing an electroencephalogram(EEG) using the correlation dimension by which the brain states can be discriminated. The method uses a time-delay determining method necessary for reconstructing vectors from the EEG time series, and a relative ratio of a correlation exponent.

2 Claims, 6 Drawing Sheets

METHOD FOR ANALYZING ELECTROENCEPHALOGRAM USING CORRELATION DIMENSION

BACKGROUND OF THE INVENTION

1. Field of the Invention

The present invention relates to a method for analyzing an electroencephalogram(EEG) using a correlation dimension, and more particularly to a method for analyzing an EEG time series by which a brain state can be determined using a time-delay determining method necessary for reconstructing vectors from the EEG time series in the embedding dimension, and a relative ratio of a correlation exponent (hereinafter, referred to as a relative correlation exponent).

2. Description of the Conventional Art

It is well known that a correlation dimension is most widely used in chaotic dynamics analyses. In analyzing the EEG(electroencephalogram) through the use of the conventional correlation dimension, the analysis method includes a first step of constructing vectors in an embedding dimension from the EEG time series by using a time delay, a second step of calculating a correlation integral for the vectors, a third step of obtaining a correlation exponent by using the local slope of the correlation integral, and a fourth step of obtaining the correlation dimension from the correlation exponent with varying the embedding dimension. For the stochastic time series, the correlation exponent continuously increases with the embedding dimension. In case of the chaotic system, the correlation exponent converges into a constant value which is referred to as the correlation dimension. Accordingly, the measurement of the correlation dimension enables one to determine whether the time series is stochastic or chaotic. Also, since the correlation dimension for the EEG during sleep and epileptic seizure is much lower than that of the normal brain state, the correlation dimension can be used in diagnosing the encephalopathy.

However, since the conventional correlation dimension measurement includes the above first step of obtaining the time delay from the specific function, such as the autocorrelation function, the dependence on the time delay of the embedding dimension is ignored. Further, at the fourth step in the above-mentioned method, it is difficult to obtain the correlation exponent in a high embedding dimension, because the number of data of the EEG time series is limited in experiments.

SUMMARY OF THE INVENTION

Accordingly, it is an object of the present invention to provide an EEG analysis method using the correlation dimension which includes determining a time delay considering the dependence on an embedding dimension of the time delay, by which the brain state can reliably be determined regardless of the limited data and difference between subjects.

To achieve the above object, there is provided a method for analyzing an EEG using a correlation dimension, wherein a first step considers the dependence of a time delay on the embedding dimension by obtaining the time delay for each embedding dimension through the use of the local slope, and wherein a fourth step obtains the relative correlation exponent for the different brain state with respect to the normal brain state, rather than the correlation dimension, consequently to solve the difference between subjects. Partial solution to the finite of experimental data is made by an easy derivation of the reliable result even in high embedding dimension using the relative correlation exponent according to the present invention.

While the conventional time-delay determining method gives a single value irrespective of the embedding dimensions, thereby causing underestimation or overestimation of the correlation exponent inevitably, the time-delay determining method according to the present invention provides the optimal time delay in each embedding dimension, resulting in the prevention of the underestimation or overestimation.

The correlation dimension gives difficulty in discriminating the brain states with reference to the average value taken over various subjects having large deviation, but this invention solves the deviation between the subjects through the use of the relative ratio between the correlation exponent obtained from the different states, considering the differences between the individual subjects.

Further, the relative correlation exponent can be used even in a high embedding dimension where the correlation dimension cannot be obtained. Therefore, the present invention is also useful for the limited data available in the clinical and experimental environment.

BRIEF DESCRIPTION OF THE DRAWINGS

The present invention will become more fully understood to following detailed description taken in conjunction with the accompanying drawings, wherein.

DETAILED DESCRIPTION OF THE INVENTION

The preferred embodiment according to the present invention will now be described in detail with reference to the accompanying drawings.

Referring to FIGS. 1A through 1E, a method for measuring the correlation dimension for an EEG time series will be explained below.

In a first step of the method according to the present invention, from the EEG time series (11) consisting of N data points, N' vectors (12) can be reconstructed in n-dimensional embedding space by using the time delay $\tau$. Here, N' is identical to N-(n-1)$\tau$. Assume that the EEG time series (11) denotes as $\{V_1, V_2, V_3, \ldots, V_{N-1}, V_N\}$. Then, the vector (12), $X_i$ in the n-dimensional embedding space are represented as the vectors having n components as follows.

$$
\begin{aligned}
X_1 &= (V_1, & V_{1+\tau}, & V_{1+2\tau}, \ldots, & V_{1+(n-1)\tau}) \\
X_2 &= (V_2, & V_{2+\tau}, & V_{2+2\tau}, \ldots, & V_{2+(n-1)\tau}) \\
X_3 &= (V_3, & V_{3+\tau}, & V_{3+2\tau}, \ldots, & V_{3+(n-1)\tau}) \\
&\;\;\vdots & \vdots & \vdots & \vdots \\
X_{N'-1} &= (V_{N'-1}, & V_{N'-1+\tau}, & V_{N'-1+2\tau}, \ldots, & V_{N'-1+(n-1)\tau}) \\
X_{N'} &= (V_{N'}, & V_{N'+\tau}, & V_{N'+2\tau}, \ldots, & V_{N'+(n-1)\tau}).
\end{aligned}
$$

Figure 1A:
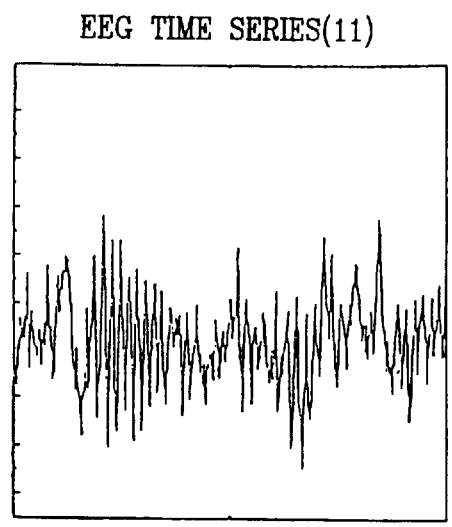
FIGS. 1A to 1E are diagrams for explaining a method for measuring a correlation dimension for an EEG time series.
Figure 1B:
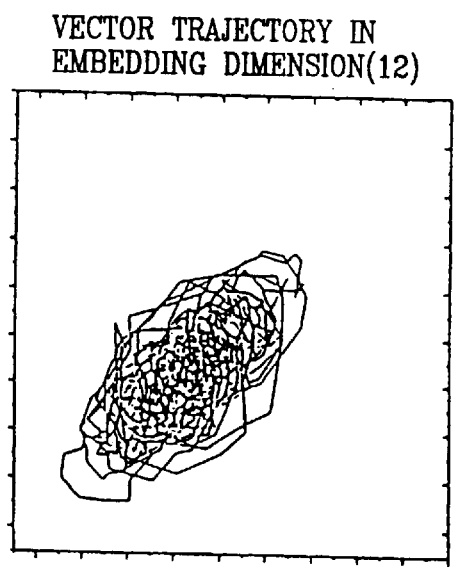
Figure 1C:
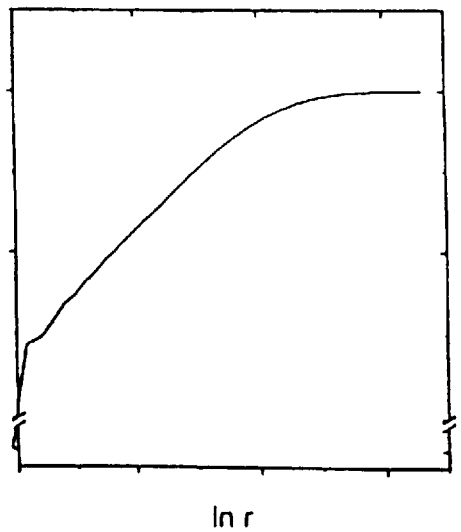
Figure 1D:
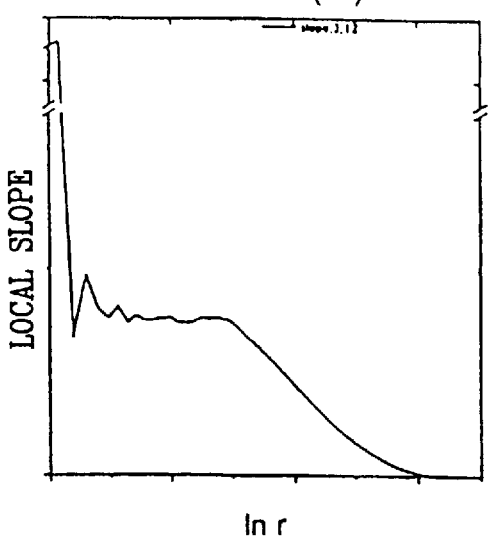
Figure 1E:
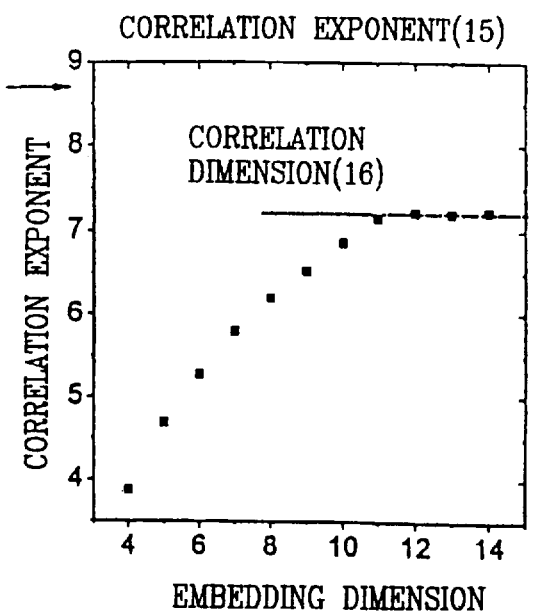

In a second step of the method of the present invention, the number of vector pairs where a distance between two vectors is smaller than a predetermined, given distance r gives the correlation integral (13), C(r)(see FIG. 1C). In a third step, the correlation integral (13) exhibits the scaling of $C(r) \sim r^d$, where the index d is the correlation exponent (15). One find flat region (hereinafter, referred to as plateau region) in the local slope (that is, the slope, d ln C(r)/d ln r) between the nearest points in a logarithmic graph for the correlation integral so as to find out a region exhibiting the above-mentioned scaling. For that region, the correlation exponent (15), d is obtained using a least square fit with reference to the logarithmic graph for the correlation integral.

Figure 2:
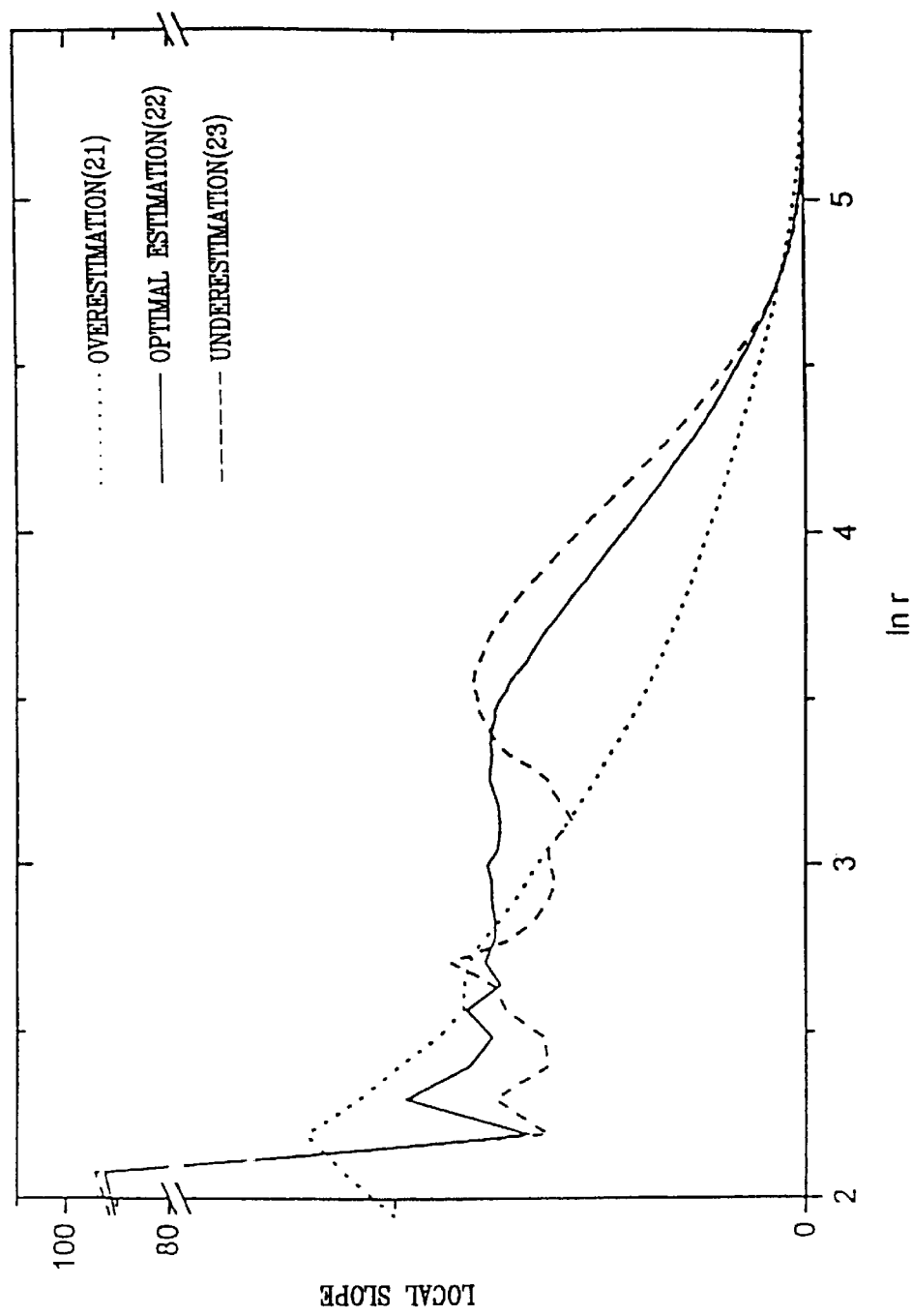
FIG. 2 shows graphically the change of local slope with time delay.

FIG. 2 graphically shows the change of local slope with time delay.

The local slope (14) varies with the time delay. As the time delay increases, the correlation exponent (15) passes through overestimation (21) and optimal estimation (22), and then finally reaches an underestimation (23). As the embedding dimension becomes larger, the time delay for the optimal estimation (22) becomes smaller. Accordingly, since the time delay obtained from the specific function, such as the autocorrelation function, or mutual information has a single value regardless of the embedding dimension, the underestimation (23) and overestimation(21) for the correlation exponent (15) cannot be avoided. According the method of the present invention, the underestimation (23) and overestimation(21) can be avoided in that using a feedback method(that is, the first step→the second step→the third step→the first step→ . . . ), the time delay is found out which maximizes the plateau region on the local slope (14) for the correlation integral (13) calculated in each embedding dimension.

At a fourth step of the preferred method, the above-described series of procedures are repeated with changing the value of the embedding dimension. In a chaotic system, not stochastic, the value of the correlation exponent (15) converges into a constant value, which is the correlation dimension (16). Since clinical or experimental EEG time series data are limited in numbers, it is difficult to find the plateau region on the local slope in a larger embedding dimension. Further, when the brain states are to be discriminated based upon the correlation dimension values obtained from the EEGs measured for the different states of the brain, the correlation dimension values are considerably different between subjects. Therefore, the correlation dimensions resulted from the average taken for the subjects exhibits large deviation, which is not suitable for the method for determining the brain states.

Instead of using the correlation dimension resulted from the average taken for the subjects, the present invention obtains the ratio of the correlation exponents obtained from different states for a subject, and then takes the average for the subjects.

Figure 3A:
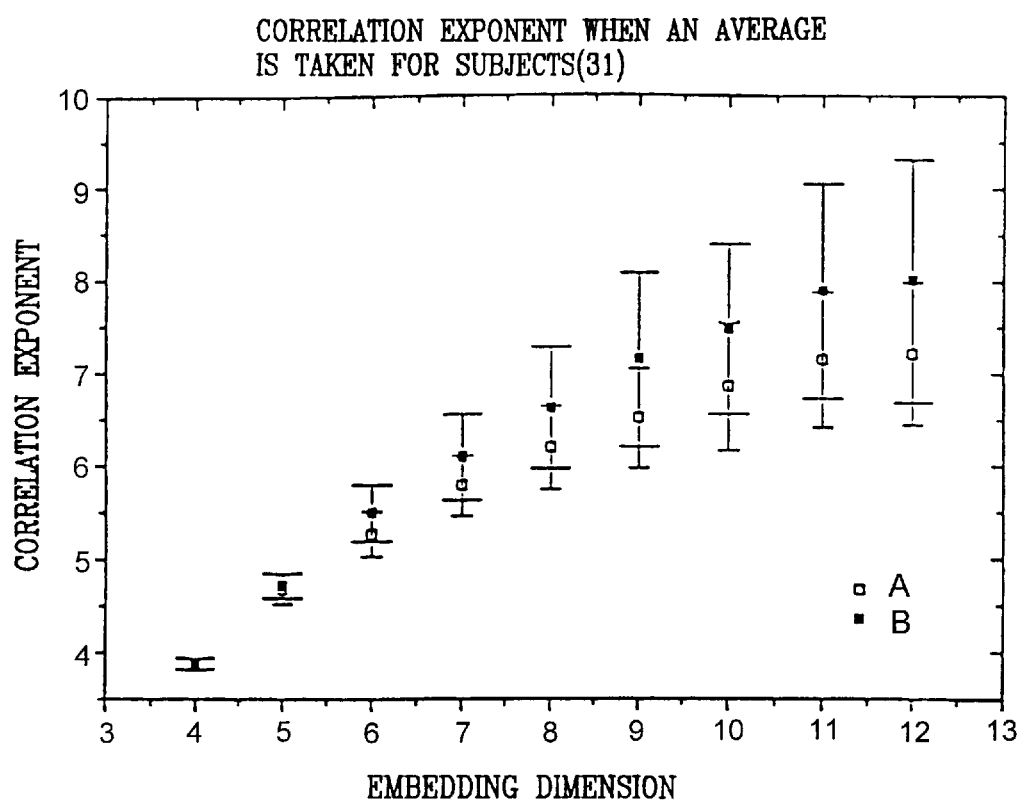
FIGS. 3A and 3B graphically show a correlation exponent and relative correlation exponent related to the EEGs for two different brain states.
Figure 3B:
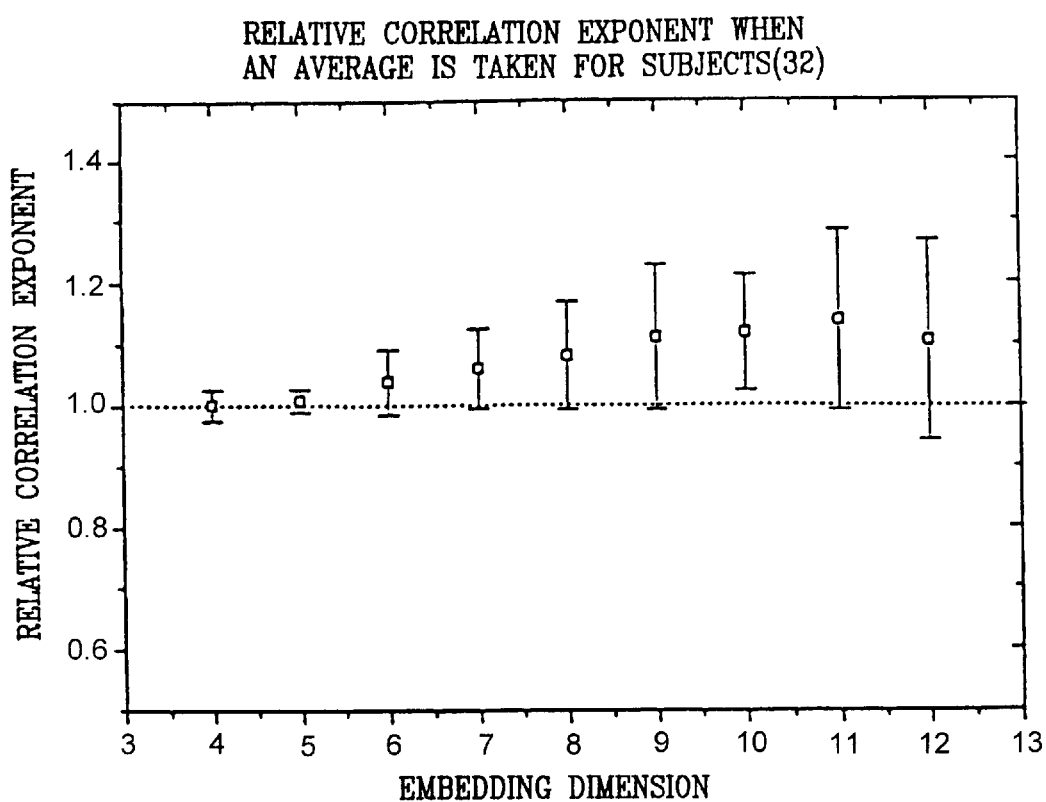

FIGS. 3A and 3B graphically show the correlation exponent and relative correlation exponent related to the EEGs for two different brain states.

These drawings show the correlation exponent (31) for the EEGs measured for two states A, B. Because the deviation between the subjects is large, the correlation dimension (or, correlation exponent) can not be used in discriminating the states A, B. The present invention obtains the relative correlation exponent (32)(dB/dA), namely, the ratio of the correlation exponent (dA) derived at the state A to another correlation exponent (dB) derived at the state B, for each individual, and then takes an average for them. Two states A and B can reliably be discriminated, although the deviations for the subjects are considered.

As shown in FIG. 3B, one can know that the relative correlation exponent (32) is larger than 1, regardless of the deviation as mentioned above. As a result, two states A and B can be discriminated from each other for individual subjects.

As described above, while the conventional time delay determining method uses a single value irrespective of the embedding dimensions, thereby causing underestimation or overestimation of the correlation exponent inevitably, the time delay determining method according to the present invention determines the optimal time delay in each embedding dimension, resulting in the prevention of the underestimation or overestimation.

The correlation dimension gives difficulty in discriminating the brain states with reference to the average value taken for the subjects owing to large deviations, but this invention solves the deviation between the subjects through the use of the relative ratio between the correlation exponents derived for the different states, considering the differences between the individual subjects.

Further, the relative correlation exponent can be used even in a high embedding dimension where the correlation dimension can not obtained. Therefore, the present invention is also useful for the limited number of data available from the clinical and experimental environment.

Accordingly, this invention can be used as a tool enabling the discrimination of the cognitive or emotional state of the normal subject.

What is claimed is:

1. A method for analyzing an electroencephalogram (EEG) using a correlation dimension, the method comprising the steps of:

reconstructing vectors in an embedding dimension by using a time delay from an EEG time series;

calculating a correlation integral from said vectors in the embedding dimension;

obtaining correlation exponents from said correlation integral;

obtaining the relative ratios between said correlation exponents obtained at different brain states for each subject;

taking an average of said relative ratios over subjects; and discriminating said different brain states by using said average of relative ratios.

2. The method as defined in claim 1, wherein an optimal time-delay is determined as maximizing a plateau region on a local slope of the correlation integral calculated from EEG time series.

* * * * *